United States Patent

Benz et al.

Patent Number: 5,982,501
Date of Patent: Nov. 9, 1999

[54] REFLECTANCE MEASURING DEVICE

[75] Inventors: Christian Benz, Wettingen; Thomas Senn, Dielsdorf, both of Switzerland

[73] Assignee: Gretag-Macbeth AG, Switzerland

[21] Appl. No.: 09/075,202

[22] Filed: May 11, 1998

[30] Foreign Application Priority Data

May 13, 1997 [EP] European Pat. Off. .............. 97107780

[51] Int. Cl.$^6$ .......................... G01N 21/47; G01N 21/55; G01J 1/02
[52] U.S. Cl. ........................... 356/446; 356/448; 356/243
[58] Field of Search .................. 356/445–448, 356/319–325, 243; 280/226

[56] References Cited

U.S. PATENT DOCUMENTS

| | | |
|---|---|---|
| 4,929,084 | 5/1990 | Mast et al. . |
| 4,961,646 | 10/1990 | Schrammli et al. . |
| 4,968,140 | 11/1990 | Berner et al. . |

FOREIGN PATENT DOCUMENTS

| | | |
|---|---|---|
| 0328483 | 8/1989 | European Pat. Off. . |
| 0331629 | 9/1989 | European Pat. Off. . |
| 0383209 | 8/1990 | European Pat. Off. . |
| 0327499 | 8/1998 | European Pat. Off. . |
| 92/15859 | 9/1992 | WIPO . |
| 96/42010 | 12/1996 | WIPO . |

OTHER PUBLICATIONS

European Search Report, 97107780.

*Primary Examiner*—Robert H. Kim
*Assistant Examiner*—Amanda Merlino
*Attorney, Agent, or Firm*—Burns, Doane, Swecker & Mathis, L.L.P.

[57] ABSTRACT

A measuring device, designed as a hand-held device, is disclosed, having a housing, an optical measuring head movably arranged in the housing for charging a test object with measuring light and for collecting light reflected by the test object, an opto-electric converter for converting the collected light into electrical signals, a computer processing the electrical signals and controlling the device, a display for displaying the measurement values obtained from the processing of the electrical signals and operating members working with the computer for controlling the device functions. Upon a triggering of the measuring process, the measuring head is moved, by a motor controller by a computer, out of a rest position into a measuring position and back into the rest position. A calibrating position is provided, in the housing, into which the measuring head can be moved and in which a calibration test object is disposed. The computer measures the calibration test object and generates calibration measurement values. Reference values corresponding to the calibration measurement values are stored in the computer. The computer performs calibration of the device by using calibration measurement values and the stored reference values. An automatic measurement of the calibration test objects in accordance with a predetermined program and a corresponding calibration or checking processes of the device can be performed. An accurate measurement of the calibration test objects is achieved as the calibration test objects are always available and cannot be confused with calibration test objects of other measuring devices.

15 Claims, 2 Drawing Sheets

REFLECTANCE MEASURING DEVICE

BACKGROUND OF THE INVENTION

1. Field of the Invention

This invention relates to a device for measuring optical reflectance values of a test object and/or measured values derived therefrom and more particularly to a spectrophotometer.

2. State of the Art

Measuring devices, such as spectrophotometers of the type of the present invention, have been described in U.S. Letters Pat. Nos. 4,968,140, 4,961,646 and 4,929,084 (corresponding to European Patent Publications EP-B-0 328 483, EP-B-0 331 629 and EP-B-0 327 499). These computer-controlled measuring devices are embodied as hand-held devices and have a movable measuring head which is extended out of a housing for the measurement process and is subsequently retracted into the housing.

As with many measuring instruments, measuring devices of the type in accordance with exemplary embodiments of the present invention need to be regularly calibrated or checked with respect to their spectral calibration if the dependability of the measured results is to be assured. This is achieved by measuring special calibration test objects (calibration standards) matched to the respective measuring device, which are provided as separate components of the measuring device. These measured values are evaluated by the computer in connection with corresponding stored reference values, in order to either obtain a statement regarding the properties of the measuring device to be checked, or to perform calibration automatically, provided the measuring device is equipped with such functions.

These calibrating and checking processes require special care and regularity. These processes must be performed within prescribed time intervals, and the positioning of the measuring device, or its measuring head, relative to the calibration test object must be correct, so as not to affect the measured results negatively.

SUMMARY OF THE INVENTION

It is an object of the present invention to improve a measuring device in such a way that calibration and checking of the device becomes simpler and more dependable for the user. In particular, it is intended that the user need not be concerned with calibration and checking, i.e. all steps are to be performed automatically by the device.

A measuring device in accordance with the invention contains at least one calibration test object which is permanently installed in the device and can be started up by the measuring head. For example, the calibration test object can be arranged in the resting position of the measuring head. It is possible, with this arrangement, to automatically measure the calibration test object(s) in accordance with a predetermined program, and to perform the respective calibration and checking functions. The measurement always takes place in a precise and consistent manner and are always available. The calibration test object(s) is (are) always available and cannot be confused with other, similar calibration test objects which are part of other measuring devices, such as often the case in connection with conventional measuring devices with separate calibration test objects.

The invention will be explained in more detail below, making reference to the drawings.

BRIEF DESCRIPTION OF THE DRAWINGS

The present invention can be further understood with reference to the following description and the appended drawings, wherein like elements are provided with the same reference numerals. In the drawings.

DETAILED DESCRIPTION OF THE PREFERRED EMBODIMENT

Figure 1:
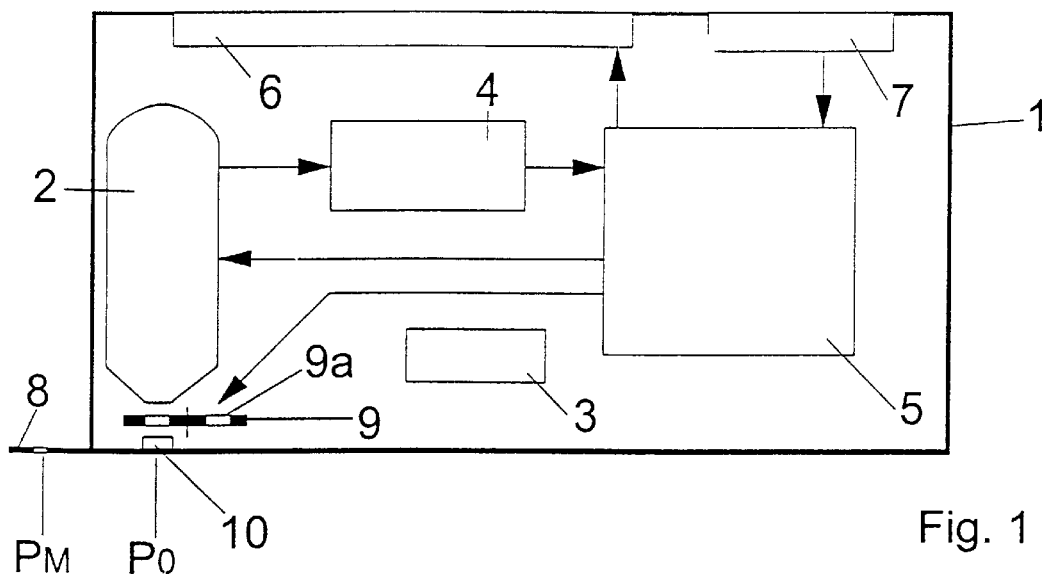
FIG. 1 illustrates a basic diagram of an exemplary embodiment of the device of the present invention.

With reference to FIG. 1, the measuring device represented, embodied as a hand-held instrument, comprises an essentially cubic housing 1 in, or on, which all other functional elements of the device are housed. Among the elements are a movable measuring head 2, a drive device 3 for moving the measuring head 2, an opto-electric converter device 4, a computer 5, a display device 6 and an operating member in the form of a keyboard 7. The housing 1 is further provided with a sighting device 8 that is used for positioning the measuring device on a test object O. A filter wheel 9, which can be moved together with the measuring head 2, is provided underneath the measuring head 2, by means of which several different filters 9a can be selectively introduced into the measuring beam path.

The measuring head 2 is normally at a resting position $P_0$ inside the housing 1. If a measuring process is triggered, for example by the actuation of an appropriate operating member, the measuring head 2 is extended by means of the drive device 3 out of the housing 1 into a measuring position $P_M$. In this position, it is located directly above the sighting device 8. At the end of the measuring process, the measuring head 2 is pushed back into its resting position $P_0$ inside the housing 1. The converter device 4, together with the measuring head 2, is located on a carriage (not shown), and it is moved together with the measuring head.

Figure 2:
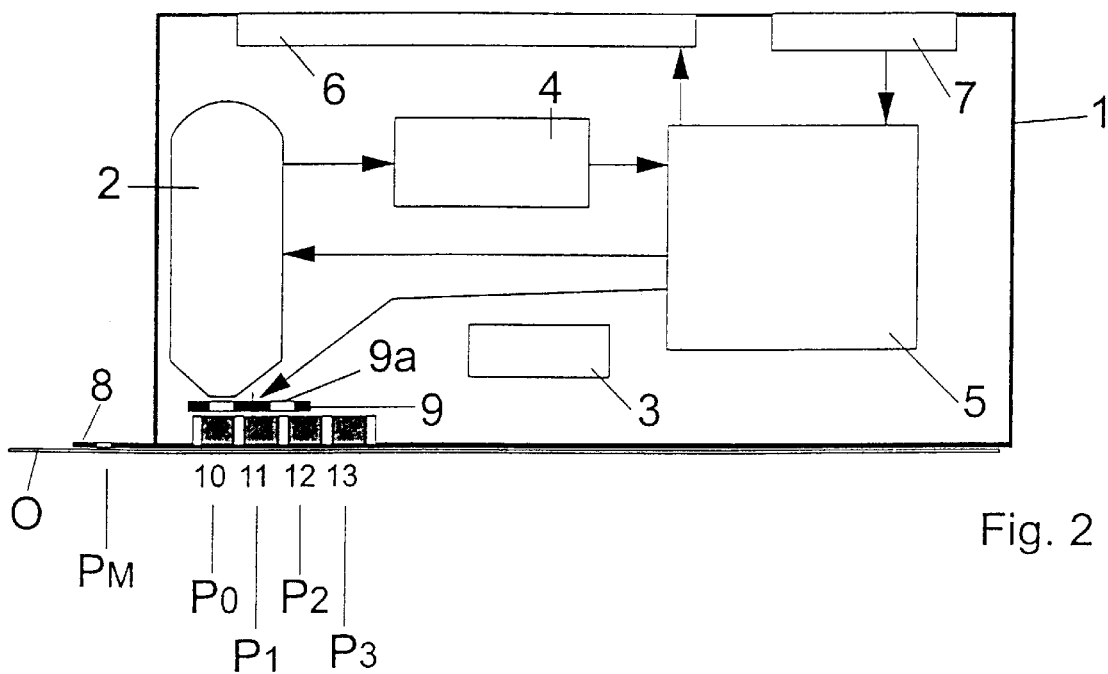
FIG. 2 illustrates a schematic representation of the device of FIG. 1 with the measuring head in the resting position.
Figure 3:
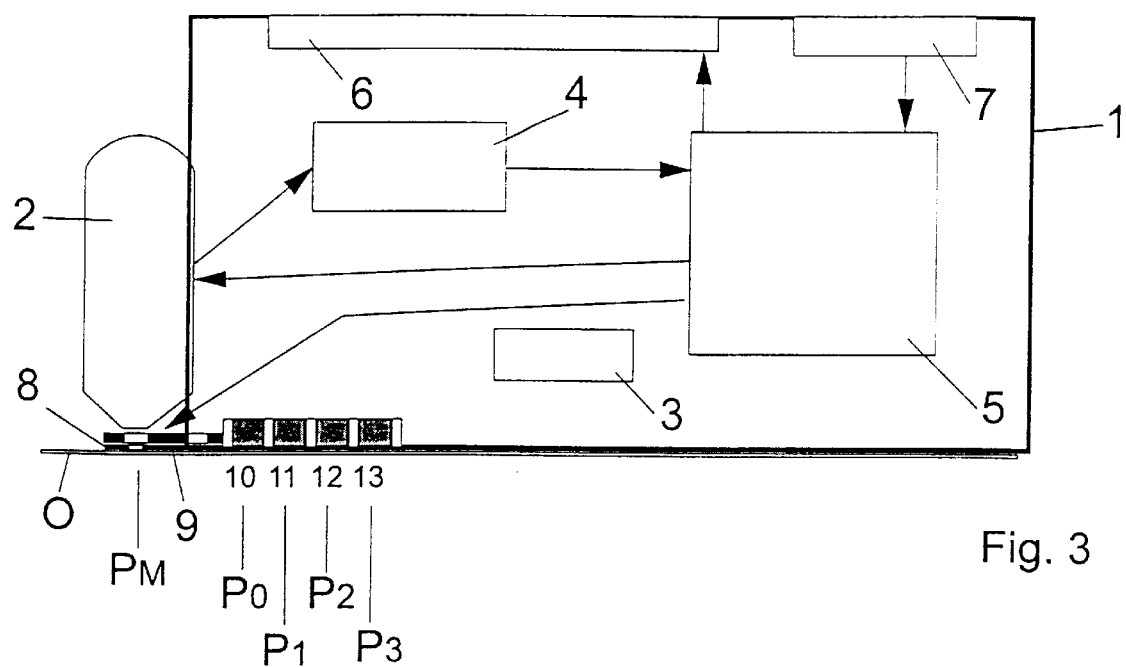
FIG. 3 illustrates a schematic representation of the device of FIG. 1 with the measuring head in the measuring position.

In the course of the measuring process, the measuring head 2 acts upon a test object O (shown in FIG. 2), positioned underneath the measuring head 2 or underneath the sighting device 8, with measuring light within a standardized angular range coming from a light source located in the measuring head, and collects the light reflected back from the test object within a standardized angular range, and passes it on to the converter device 4. In the process, it is possible to affect the spectral composition of the measuring light and of the collected reflected light in the manner required for the type of measurement selected by means of positioning one of the filters 9a of the filter wheel 9. If desired, positioning of the filters 9a can also take place only in the illumination beam path or only in the collected beam path, wherein just the measuring light or only the reflected light would be affected. The collected light is spectrophotometrically analyzed in the converter device 4, i.e. the reflectances are measured, for example, in 36 wave length areas of approximately 10 nm width in the visible range of the spectrum (380 to 730 nm) and converted into corresponding electrical signals. These signals are then transmitted to and processed by the computer 5 to determine the measured values of interest for the respective measurement, such as, color coordinates in accordance with CIE. These measured values are then output on the display device. All measuring functions and mechanical sequences of the device are controlled by the computer 5.

To this extent, the measuring device shown completely corresponds in its structure and function to the hand-held spectrophotometer described in detail in U.S. Letters Pat. Nos. 4,968,140, 4,961,646 and 4,292,084 mentioned at the outset, so that one skilled in the art will not require any more detailed explanation. The subject matter of these patents is hereby incorporated by reference.

The measuring device in accordance with exemplary embodiment of the present invention is equipped with a series of internal calibration test objects, indicated by 10,11, 12 and 13, which are arranged inside the housing in appropriate calibration measuring positions, indicated by $P_0$, $P_1$, $P_2$ and $P_3$. In the exemplary embodiments illustrated, one of these calibration measuring positions could also be the resting position of the measuring head, but need not necessarily be so. The drive device 3, as controlled by the computer 5, can selectively displace and position the measuring head 2 into each one of the calibrating measuring positions $P_0$, $P_1$, $P_2$ and $P_3$. At the same time, the computer 5 is programmed to trigger and perform a measuring operation in each one of these calibration measuring positions $P_0$, $P_1$, $P_2$ and $P_3$, the same as in the measuring position $P_M$. The calibration test objects 10 to 13 are arranged in the housing 1 in such a way that they take up the same position in relation to the measuring head, which is in the calibration measuring position, as the test object O when the measuring head is in the measuring position $P_M$.

The internal calibration test objects 10, 11, 12 and 13, according to exemplary embodiments of the present invention are arranged in the housing 1 of the device, can be different reference objects depending on the intended use. A white standard is required for an absolute white calibration, different color standards are employed for checking the spectral calibration. It is also possible to employ densitometric test tiles as calibration test objects. By means of the calibration test objects built in accordance with the invention into the housing, it is possible to perform the measurements of the calibration test objects required for the various calibration and checking processes automatically in a time-, event or user-controlled manner.

It is assumed that a white standard for the absolute white calibration of the measuring device is located in the resting position, which is also is the calibrating position $P_0$, and one color standard from 11 to 13 in the remaining calibrating positions $P_1$ to $P_3$ for checking the spectral calibration of the measuring device. If only the absolute white calibration, or only checking of the spectral calibration are required, the unwanted calibration test objects can be omitted. It is, of course, also possible to select a different arrangement of the individual calibration test objects 10 to 13 in the calibration measuring positions $P_0$ to $P_3$. Furthermore, other calibration test objects can also be provided for different types of checking.

With appropriate programming, the computer 5 can, for example, perform an automatic absolute white calibration immediately prior to each measuring process. It is possible to correct the instability of the light source in the measuring head and to obtain a stabilization of the measured values. If, for example, a measuring process is manually triggered by the user, the measuring head initially is still in the resting position $P_0$ above the white standard 10. The computer 5 first causes the measurement of the white standard 10 and the automatic absolute white calibration. Thereafter, the measuring head 2 is extended into the measuring position $P_M$ and measurement of the test object O is performed. Subsequently, the measuring head is moved back into the resting position $P_0$. The measurement results are calculated and displayed.

For the absolute white calibration, the white standard 10 is measured, and the calibration measurement values obtained in the course of this, along with the reference values stored in the computer 5, are used in a known manner for the automatic calibration of the device. As noted, automatic calibration takes place in a conventional manner.

Measurement of the white standard for the absolute white calibration can also take place by means of one or several of the filters 9a of the filter wheel 9. If the device has been correctly set, for example prior to or shortly after delivery, the calibration measurement results obtained thereby can also be stored in the computer as reference measurement values for the later use in accordance with the above description. To this end, the measuring device is equipped with a corresponding operating mode.

One option of checking the spectral calibration, and therefore the correct setting and the dependability of the measuring device, consists in measuring the white standard 10, for example, by means of a so-called band glass provided in the filter wheel 9. A suitable band glass, for example, is the type BG 36 of the Schott Company. In the course of this measurement, the spectral reflectances of the white standard are determined as calibration measurement values and compared with the corresponding stored reference measurement values. A deviation value is selected as quality criteria which, for example, is calculated as the square root of the sum of the squares of the differences between the measured calibration measurement values and the stored reference measurement values. If the deviation value lies above a predetermined tolerance threshold, the computer 5 indicates this in a suitable manner, for example by an appropriate alarm notice, by means of the display device 6. Alternatively or additionally, the alarm notice can be transmitted to an external computer via the interface, which is customary in modern measuring device of this type.

The spectral calibration of the measuring device can also be checked by means of the color standards 11 to 13. To this end the color standards are spectrally measured and their respective color coordinates are determined, for example in accordance with CIELAB, as calibration measurement values. These color coordinates are compared with the appropriate stored reference color coordinates of the color standards, and the respective color difference is determined. If one or several of the color differences determined in this manner lies above a predetermined tolerance threshold, the computer 5 generates an appropriate alarm notice. This check, too, can take place at different positions of the filter wheel 9, i.a. with different filters 9a. Incidentally, the filters 9a are conventional filters, customarily employed with such measuring processes, for example UV-cut filters, D65 filters, polarizing filters and the like.

A check of the linearity of the measuring system of the device is also possible by measuring a density stage wedge (gray stage wedge), which can be realized, for example, by means of calibration test objects in the form of one black tile, two gray tiles and one white tile. The spectral reflectances over the visible spectral range are measured for each one (here, for example, four) of the tiles (calibration test objects) of the gray stage wedge and are compared with the corresponding stored reference values. As a measure of quality, a value Kj is formed for each wavelength range j in accordance with the equation:

$$Kj = \sqrt{\sum_{i=1}^{4} (R_{Mij} - R_{Sij})^2}$$

wherein RMij and RSij are the spectral reflectance values measured at the tile i, or the corresponding stored reference values for the wavelength j. If one or several of the values Kj exceeds a defined tolerance limit, an appropriate alarm notice is issued.

As noted, the automatic calibration can also take place in a time- or event-controlled manner. For example, the computer 5 can be programmed in such a way that it performs a check or calibration at defined time intervals, or after a defined number of measurements.

It will be appreciated by those skilled in the art that the present invention can be embodied in other specific forms without departing from the spirit or essential characteristics thereof. The presently disclosed embodiments are therefore considered in all respects to be illustrative and not restrictive. The scope of the invention is indicated by the appended claims rather than the foregoing description and all changes that come within the meaning and range and equivalence thereof are intended to be embraced therein.

What is claimed is:

1. A device for measuring optical reflectance values and displaying at least one of optical reflectance values and measured values derived from said reflectance values of a test object, comprising:

a housing;

an optical measuring head movably arranged in said housing for charging said test object with a measuring light and collecting light reflected by the test object;

an opto-electric converter for converting the light collected by the measuring head into corresponding electrical signals;

a computer, for controlling said device, processing the electrical signals to obtain a set of measurement values, said computer storing a plurality of reference values corresponding to a set of calibration measurement values;

a display means for displaying the measurement values obtained from said processing; and an operating means operatively connected with said computer for controlling functions of said device such that, upon a triggering of a measuring process, the measuring head is moved out of a rest position by a motor into a measuring position and back into the rest position, said measuring position including at least one calibrating position having a calibration test object disposed therein, and said measuring head being controlled by said computer to measure said calibration test object and to generate a set of calibration measurement values, said computer performing a calibration of said device using the calibration measurement values and said stored reference values.

2. The device of claim 1 wherein said measuring position comprises:

at least two calibrating positions into which said measuring head can be moved by said motor and controlled by said computer; and a calibration test object disposed in each of said calibrating positions, such that said computer measures and generates calibration measurement values for each test object and said computer performs a calibration of said device by means of the calibration measurement values and stored reference values for each test object.

3. The device of claim 2 wherein said computer automatically performs a measurement of each calibration test object by a triggering means controlled by at least one of: a user, a time controlled manner, and an event controlled manner.

4. The device of claim 2 wherein at least one of said calibration test objects is a white standard.

5. The device of claim 2 wherein at least one of said calibration test objects is a color standard.

6. The device of claim 2 wherein a plurality of said calibration test objects are embodied together as a density stage wedge.

7. The device of claim 2 wherein said measuring head is equipped with at least one optical filter controlled by said computer, said filter being selectively inserted into at least one of an illumination path and a collecting path during measurement of at least one of the calibration test objects.

8. The device of claim 2 wherein said measuring head is equipped with at least two different optical filters controlled by said computer, said filters being selectively inserted into at least one of an illumination path and a collecting path during measurement of at least one of the calibration test objects.

9. The device of claim 7 wherein said filter is a band glass.

10. The device of claim 2 wherein said computer stores said calibration measurement values as said reference values.

11. The device of claim 2 wherein said computer compares said calibration measurement values with said reference values and displays a result of said comparison.

12. The device of claim 2 wherein said device is a spectrally measuring color device.

13. The device of claim 12 wherein one of said calibration test objects is a color standard and said calibration measurement values and said reference values are color coordinates, and wherein a result of comparing the reference values to the measurement values is a color difference.

14. The device of claim 12 wherein one of said calibration test objects is a white standard and said calibration measurement values and said reference values are spectral reflectance values, and wherein a result of comparing the reference values to the measurement values is a square root of a sum of squares of a difference between the measurement values and the spectral reflectance values.

15. The device of claim 12 wherein a plurality of calibration test objects are embodied together as a density stage wedge and said measurement values and said reference values are spectral reflectance values, and wherein a result of comparing the reference values to the measurement values for each spectral range is a quality measurement which is a square root of a sum of squares of a difference between the measurement values measured in a spectral range at the calibration test objects and the corresponding stored reference values.

* * * * *